United States Patent [19]

Kastan

[11] Patent Number: 5,221,266
[45] Date of Patent: Jun. 22, 1993

[54] PROTECTION MEANS FOR TWO-PIECE NEEDLE

[76] Inventor: David J. Kastan, 5629 Powder Horn Dr., West Bloomfield, Mich. 48322

[21] Appl. No.: 861,444

[22] Filed: Apr. 1, 1992

[51] Int. Cl.$^5$ ............................................... A61M 5/32
[52] U.S. Cl. ................................................... 604/192
[58] Field of Search ..................... 128/749, 751, 754; 604/192, 198

[56] References Cited

U.S. PATENT DOCUMENTS

| | | |
|---|---|---|
| 4,955,866 | 9/1990 | Corey .................................. 604/192 |
| 5,051,109 | 9/1991 | Simon .................................. 604/192 |

*Primary Examiner*—Max Hindenburg
*Attorney, Agent, or Firm*—Weintraub, DuRoss and Brady

[57] ABSTRACT

A device for safely taking bodily samples is taught. A stylet is held within a sheath and cap. The cap has biased flanges at the forward end thereof to prevent inadvertent forward extension and possible contamination with the stylet to a health care worker. The flanges are formed such that the needle is forwardly extendable past the flanges initially for use. Once retracted, the flanges prevent re-extension beyond offering protection to the user or other personnel. A strap connected to the stylet and the cap prevents the separation of the stylet from the cap. The cap is detachable from the sheath, thus allowing the stylet and the cap to be withdrawn leaving the sheath for use. The stylet would only be used once and discarded with the protective cap over the sharp end of the stylet. A fresh stylet and cap could be obtained for use with the original sheath if additional procedures with the same sheath is necessary.

1 Claim, 1 Drawing Sheet

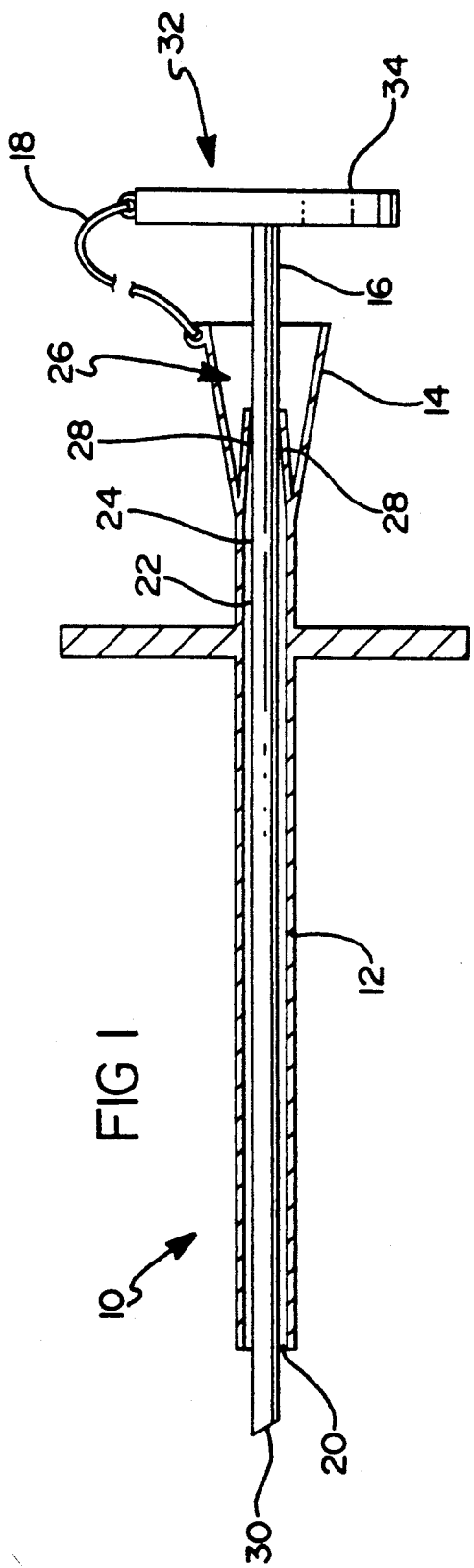
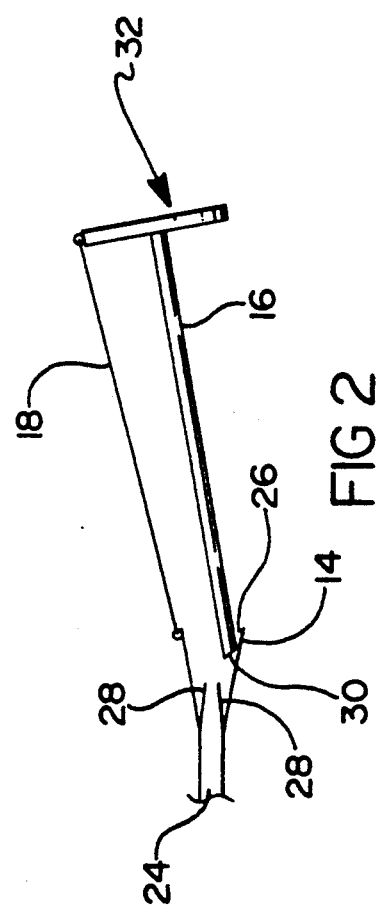

PROTECTION MEANS FOR TWO-PIECE NEEDLE

BACKGROUND OF THE INVENTION

1. Field of the Invention:

The present invention concerns the protection of health care workers. More particularly, the present invention concerns means for preventing the inadvertent injury or infection of a health care workers from infected needles, stylets or cannulas in a two-piece needle.

2. Prior Art:

Health care workers today are at great risk of injury or infection with many serious diseases, including AIDS, by contamination from sample-taking instruments. A health care worker can inadvertently injure him/herself with an infected needle. Thus, protection from inadvertent contamination is needed.

Known devices have centered around preventing inadvertent infection in the use of a hypodermic syringe, or a one-piece needle. One such device is set forth in U.S. Pat. No. 4,929,237, issued May 29, 1990 to Medway. Medway teaches a spring-biased needle cover disposed at the front end of the syringe and encompassing the needle. The needle extends beyond the protection cover by a forward thrust. The needle is then withdrawn within the cover. During the injection process, the cover contacts the skin. This contact allows the extension of the needle over the biasing force of the spring. The biasing action of the spring disposed within the cover keeps the cover in place over the needle after the injection. Thus, by the action of the spring, the chance of an inadvertent injection is greatly lessened.

U.S. Pat. No. 4,897,083 issued Jan. 30, 1990 to Martell teaches a telescoping cover disposed around the tubular body of a syringe. The telescoping cover of Martell allows for a shield to be extended around the needle after use. Other similar means are set forth with the following U.S. Patents: U.S. Pat. Nos. 4,985,021; 5,011,479; 4,425,120; 5,024,616; 4,966,592.

Despite these references, their teachings, Applicant knows of no means for protecting users of instruments containing two-piece needles. These are common medical instruments for procedures involving vascular access or fluid/tissue removal. These devices are a source of injury and infection to medical health care workers. The freedom of movement needed to perform biopsies and other procedures unique to two-piece needles necessitate different protective means than those known for single needle instruments. In addition, these prior devices are not applicable to two-piece needles. It is to this need that the present invention is directed.

SUMMARY OF THE INVENTION

The present invention concerns a device for safely taking bodily samples from a patient or obtaining access to a bodily space, the device comprising:

(a) a hollow tubular sheath having a sharp forward end and a rearward end;

(b) a cap connected to the sheath at the rearward end thereof;

(c) a stylet having a sharp forward end, the stylet being circumferentially disposed within the sheath and cap; and (d) at least one biased flange disposed within the cap; and (e) a strap connected at a first end to the sheath and at a second end to the stylet, the length of the strap restricting retraction of the stylet and allowing the capping of the forward end of the stylet;

wherein the stylet is extended beyond the biased flanges to collect a sample, the stylet being then retracted behind the at least one biased flange, the cap being detachable from the sheath and the strap preventing retraction of the needle.

For a more complete understanding of the present invention, the following detailed description should be read in conjunction with the accompanying drawings. Throughout the following description and in the drawings, like reference numerals refer to like parts.

BRIEF DESCRIPTION OF THE DRAWINGS

FIG. 1 shows a cross-sectional side view of a preferred embodiment of the device for safely taking tissue samples of the present invention, wherein the stylet is forwardly extended; and FIG. 2 shows a cross-sectional side view of the first embodiment, where the cap is detached from the sheath and the stylet is fully retracted;

DETAILED DESCRIPTION OF THE PREFERRED EMBODIMENT

Referring now to FIGS. 1 and 2, the preferred embodiment of the present invention is shown, to wit, a two-piece needle device 10 for safely obtaining bodily samples, such as tissue, fluid or cellular samples, from a patient or obtaining access to a bodily space. The device 10 can also be utilized to obtain vascular access in a patient. The device 10 comprises a sheath 12, a cap 14, a stylet 16 and a connecting strap 18.

The sheath 12 comprise a hollow tubular member formed of stainless steel or other suitable material, such as durable plastic. The sheath 12 has a sharp forward opening 20 and a rearward opening 22, the sheath 12 being one needle in the two-piece needle device 10. The sheath 12 allows fluid, tissue or cellular samples to be taken, or to obtain access to a bodily space, such as a blood vessel, where further intervention is necessary. The rearward opening 22 may have a syringe connected thereon for receiving fluid samples. The sheath 12 is designed to allow both aspiration techniques as well as access techniques, such as the passage of a wire, for further intervention.

The cap 14 comprises a generally conical body. The cap 14 has a forward opening 24 and a rearward opening 26. The cap 14 is connected to the sheath 12, such that the rearward opening 22 of the sheath 12 is in communication with the forward opening 24 of the cap 14. The cap 14 is removably connected to the sheath 12, as will be more fully described herein below.

At least one biased flange 28 is disposed within the interior of the cap 14. FIGS. 1 and 2 show a pair of flanges 28 are formed into the cap 14 proximate to the forward opening 24. More than flanges could also be used, such as four flanges in a pyramid structure. The flanges 28 extend toward the rear of the cap 14, and are biased such that the rearward ends of the flanges 28 contact each other substantially at the central axis of the cap 14. The flanges 28 prevent re-exposure of the device to health care workers or other people after a samples has been taken, as will be described more fully herein below.

Alternately, the cap 14 could have a cover (not shown) to enclose the forward opening 24 of the cap 14. The cover envisioned would snugly fit over the forward end of the cap 14 when detached from the sheath 12. Other equivalent structure can be elected, as desired.

The stylet 16 comprises a tubular instrument having a sharp forward end 30 for piercing tissue of a patient (not shown) and a rearward end 32. The stylet 16 may be formed of stainless steel or other suitable material. The stylet may additionally have a knob 34 disposed proximate the rearward end 32 for ease of handling, if desired.

The stylet 16 is disposed within the device 10 such that the stylet 16 is substantially disposed along the central axis of the sheath 12 and cap 14. The stylet 16 has a length greater than that of the sheath 12 and cap 14, such that the stylet 16 may be extended beyond both the forward opening 20 of the sheath 12 and the rearward opening 26 of the cap 14 simultaneously.

The connecting band 18 is formed of thread, cloth or other suitable material. The critical criteria in the selection of the material with which to form the strap 16 is its ability to allow free movement of the stylet 16 during the use of the device. The length and possible elasticity must maintain coverage by the cap 14 over the forward end 30 of the style 16. Ideally, the strap 18 is unrealistic.

The strap 16 is connected at a first end to the cap 14, proximate to the rearward opening 26 thereof, and at a second end to the rearward end 32 of the stylet 16. The connecting strap 18 is formed to a length that is less than that of the stylet 16. The connecting strap 18 is formed such that the stylet 16, when withdrawn fully into the cap 14, has its sharp end 30 enclosed and the sharp end 30 will not be exposed outside of the cap 14.

The utilization of the present invention will now be described. When the device 10 is used in a bodily sample taking procedure, the forward opening 20 of the sheath 12 is positioned proximate to the area of the patient (not shown) where the sample is to be extracted. The sheath 12 may then have its sharp forward end 20 inserted into the patient (not shown). The stylet 16 is next extended beyond the forward opening 20 of the sheath 12, such that the sharp forward 30 end also pierces the tissue of the patient. The stylet 16 is withdrawn into the sheath 12 by the health care work pulling rearward at the rearward of the stylet 16. The stylet 16 is then fully withdrawn through the sheath 12, such that the sharp end 30 of the stylet 16 is pulled within the cap 14. The sharp end 30 of the stylet 16 is pulled past the biased flanges 28 of the cap 14. The flanges 28 then come into contact with each other, and prevent the forward reassertion of the sharp end 30 of the stylet 16 through the forward opening 24 of the cap 14. Thus, the sharp end of the stylet 16 cannot again contact another person and thereby infect him or her. The sheath 12 may then be used for tissue sampling or access to a bodily space, or removed.

The connecting strap 18 restricts the rearward retraction of the stylet 16 relative to the cap 14. As can be seen in FIG. 2, the strap 18, when fully extended, cooperates with the cap 14, such that the stylet 16 may be not expose its sharp forward end 30 past the rearward opening 26 of the cap 14. Thus, the device 10 is completely encapsulated and protects both the health care worker and other persons from infection or injury.

The sheath 12, while still deployed in a patient, could allow a second clean stylet with an associated strap and cap 14, to be mounted thereon and deployed. This "clean" stylet could then be reinserted into the original sheath 12 for an additional use, and be removed as previously described.

Having, thus, described the invention, what is claimed is:

1. A two-piece needle device for safely taking bodily samples from a patient by allowing access to a bodily space, the device comprising:
   (a) a hollow tubular sheath having a sharp forward opening end and a rearward opening end,
   (b) a substantially conical cap having a forward opening end and a rearward opening end, the cap being connected to the sheath such that the forward opening end of the cap and the rearward opening end of the sheath communicate, the cap further having a pair of biased flanges deployed therewithin proximate the forward opening end;
   (c) a stylet having a forward end and a rearward end the stylet being removably disposed through the cap; and
   (d) a strap connected at a first end to the cap and at a second end to the rearward end of the stylet, the strap being inelastic;

wherein the biased flanges cooperate to block the forward opening end of the cap when the stylet is withdrawn within the forward opening end of the cap.

* * * * *